United States Patent
Betser et al.

(10) Patent No.: US 9,034,035 B2
(45) Date of Patent: May 19, 2015

(54) ACCOMMODATING INTRAOCULAR LENS ASSEMBLY

(75) Inventors: Nir Betser, Yahud (IL); Ehud Assia, Tel-Aviv (IL)

(73) Assignee: Mor Research Applications Ltd., Tel-Aviv (IL)

( * ) Notice: Subject to any disclaimer, the term of this patent is extended or adjusted under 35 U.S.C. 154(b) by 0 days.

(21) Appl. No.: 13/634,883

(22) PCT Filed: Mar. 14, 2011

(86) PCT No.: PCT/US2011/028256
§ 371 (c)(1),
(2), (4) Date: Sep. 14, 2012

(87) PCT Pub. No.: WO2011/115860
PCT Pub. Date: Sep. 22, 2011

(65) Prior Publication Data
US 2013/0006353 A1  Jan. 3, 2013

Related U.S. Application Data

(60) Provisional application No. 61/314,180, filed on Mar. 16, 2010.

(51) Int. Cl.
*A61F 2/16* (2006.01)

(52) U.S. Cl.
CPC ............ *A61F 2/1624* (2013.01); *A61F 2/1602* (2013.01); *A61F 2/1613* (2013.01); *A61F 2250/0008* (2013.01); *A61F 2/1635* (2013.01)

(58) Field of Classification Search
CPC ....... A61F 2/16; A61F 2/1602; A61F 2/1613; A61F 2/1624; A61F 2/1629; A61F 2/1635; A61F 2002/1605; A61F 2002/1697; A61F 2250/0003; A61F 2250/0008; A61F 2250/0013; A61F 2002/1695

USPC ........................... 623/6.13, 6.22, 6.34
See application file for complete search history.

(56) References Cited

U.S. PATENT DOCUMENTS

| 4,932,966 A | 6/1990 | Christie et al. | |
|---|---|---|---|
| 2002/0151973 A1* | 10/2002 | Arita et al. | 623/6.22 |

(Continued)

FOREIGN PATENT DOCUMENTS

| WO | 2009/015226 | 1/2009 |
|---|---|---|

OTHER PUBLICATIONS

PCT Search Report PCT/US2011/028256, Nov. 25, 2011.
International Preliminary Report on Patentability Dated Sep. 27, 2012 From the International Bureau of WIPO Re. Application No. PCT/US2011/028256.

(Continued)

*Primary Examiner* — Randy Shay

(57) ABSTRACT

An accommodating intraocular lens (AIOL) assembly (10) including an optics assembly (12) including an inflatable member (14), and characterized by an extra-capsular-bag interface structure (16) for interfacing with ocular structure of an eye external to a capsular bag for implanting the AIOL (10) outside the capsular bag, the extra-capsular-bag interface structure (16) including a less-rigid portion (18) and a more-rigid portion (20) that define a volume therebetween which is at least partially filled with a fluid (22) and which is in fluid communication with the inflatable member (14) via at least one conduit (24), and wherein the less-rigid portion (18) is responsive to movement of the ocular structure to apply a pumping force on the fluid (22) to cause the fluid (22) to flow via the at least one conduit (24) to the inflatable member (14) so as to change the optical power of the optics assembly (12).

18 Claims, 4 Drawing Sheets

(56) References Cited

U.S. PATENT DOCUMENTS

2004/0148022 A1* 7/2004 Eggleston .................... 623/6.22
2007/0129798 A1 6/2007 Chawdhary
2008/0039937 A1 2/2008 Obrebski
2009/0005865 A1 1/2009 Smiley
2009/0043384 A1 2/2009 Niwa
2009/0264998 A1 10/2009 Mentak

OTHER PUBLICATIONS

International Search Report and the Written Opinion Dated Nov. 25, 2011 From the International Searching Authority Re. Application No. PCT/US2011/028256.
Communication Pursuant to Article 94(3) EPC Dated Mar. 19, 2015 From the European Patent Office Re. Application No. 11749583.8.

* cited by examiner

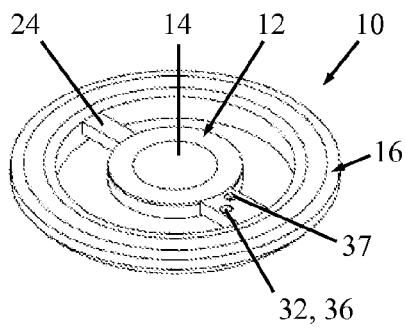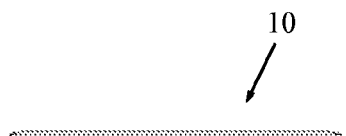
FIG. 1A  FIG. 1B
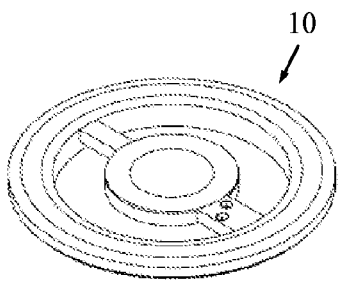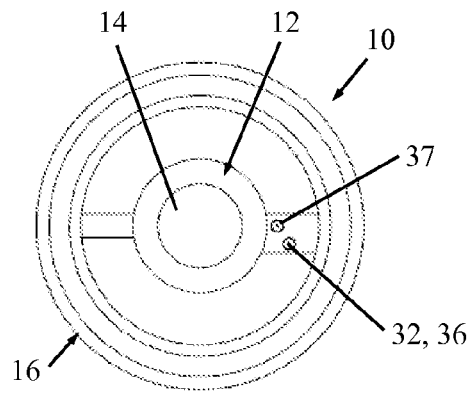
FIG. 2A  FIG. 2B
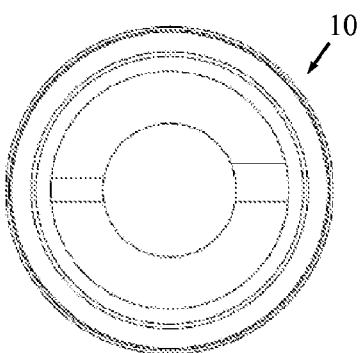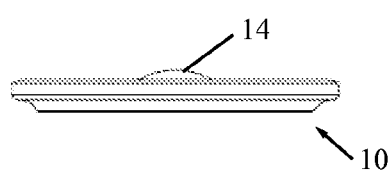
FIG. 2C  FIG. 2D
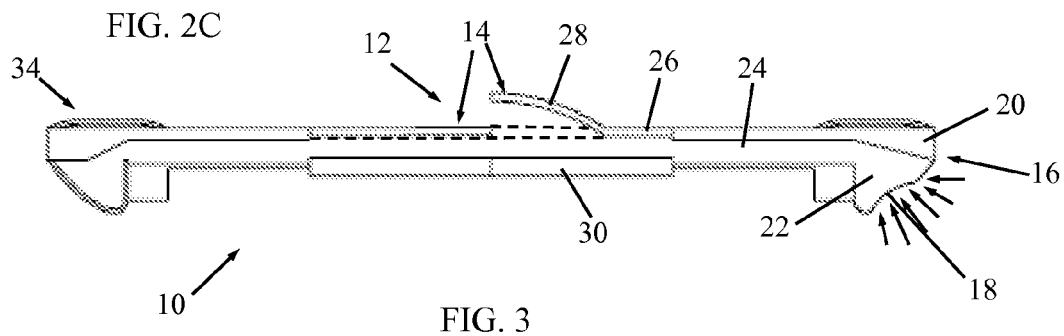
FIG. 3

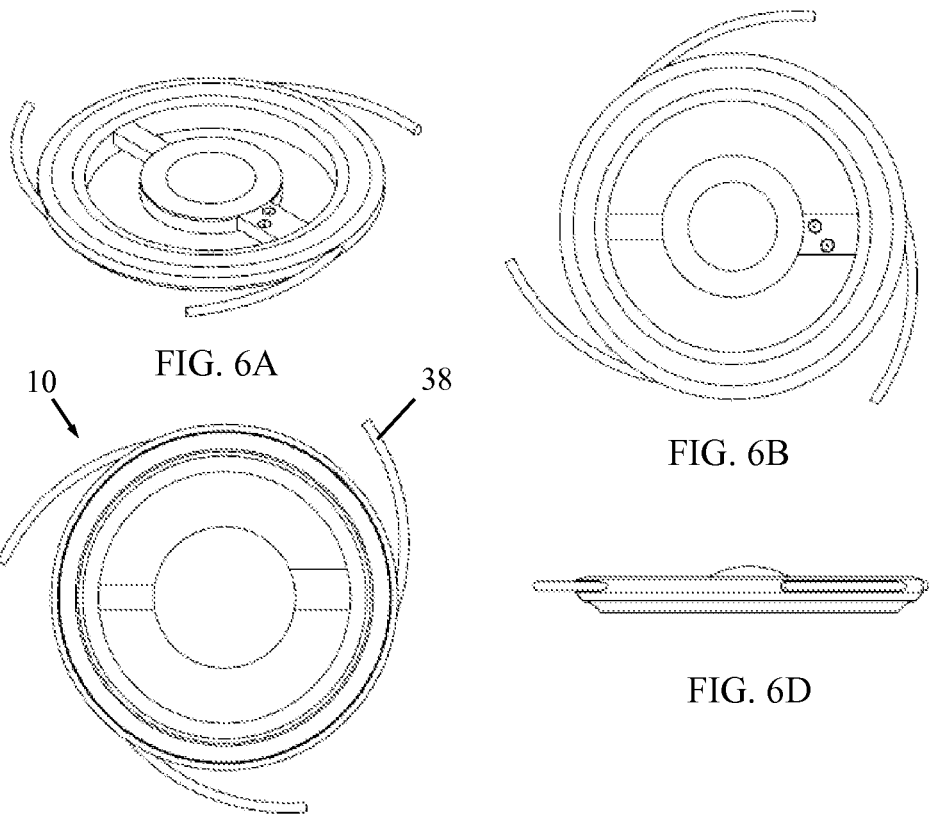
FIG. 6A
FIG. 6B
FIG. 6C
FIG. 6D
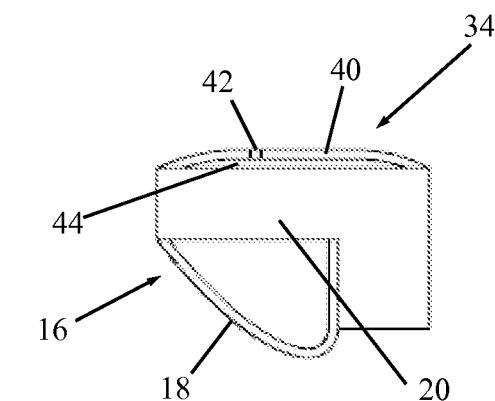
FIG. 7

US 9,034,035 B2

ACCOMMODATING INTRAOCULAR LENS ASSEMBLY

FIELD OF THE INVENTION

The present invention generally relates to accommodating intraocular lenses.

BACKGROUND OF THE INVENTION

Intraocular lenses (IOLs) have been in use for more than 60 years as an implanted replacement for the natural lens in the human eye after cataract surgery. Until the age of 40, the natural lens can change its curvature shape, and as a result its optical power, for sharp vision of far and near objects in a process called accommodation.

Despite there being many accommodative intraocular lenses (AIOL) in the prior art, currently there is only one FDA approved AIOL and other AIOLs are in different phases of development. None of these AIOLs shows sufficient and continuous accommodation (change of optical power to focus on distance and near objects) with great optical quality.

SUMMARY OF THE INVENTION

An aspect of some embodiments of the invention relates to an accommodating intraocular lens (AIOL) assembly comprising: an optics assembly comprising an inflatable member that has non-zero optical power when inflated; and an extra-capsular-bag interface structure for interfacing with ocular structure of an eye external to a capsular bag for implanting the AIOL outside the capsular bag, the extra-capsular-bag interface structure comprising a less-rigid portion and a more-rigid portion that define a volume therebetween which is at least partially filled with a fluid and which is in fluid communication with the inflatable member via at least one conduit, and wherein the less-rigid portion is responsive to movement of the ocular structure to apply a pumping force on the fluid to cause the fluid to flow via the at least one conduit to the inflatable member and change an inflation level of the inflatable member so as to change the optical power of the optics assembly, and wherein the less-rigid portion is posterior relative to a first portion of the more-rigid portion, posterior defined along an anterior-posterior optical axis of the AIOL assembly, the less-rigid portion is curved and the first portion of the more-rigid portion is flat; the more rigid portion further comprising an extension in a posterior direction which is at a radially inward position relative to the less rigid portion. In some embodiments, the less-rigid portion and the more-rigid portion are part of an at least partial tubular ring. In some embodiments, the AIOL further comprises a capsular bag IOL, wherein the optics assembly serves as an additional lens to the capsular bag IOL. In some embodiments, the inflatable member comprises a plano lens covered by a central membrane. In some embodiments, the optics assembly comprises in addition to the inflatable member a lens with non-zero optic power. In some embodiments, the AIOL assembly further comprises a regulation mechanism to adjust optical power of the optics assembly. In some embodiments, the AIOL assembly comprises an adjustment mechanism to change a position of the AIOL assembly along an optical axis of the eye. In some embodiments, the AIOL assembly comprises an adjustment mechanism to change a position of the AIOL assembly with respect to an iris of the eye. In some embodiments, the less-rigid portion is concave facing away from the inflatable member during application of the pumping force, whereas a first flat portion the more-rigid portion remains flat and generally parallel to a deflated anterior face of the inflatable member. In some embodiments, the inflatable member comprises a lens surface and inflation of the inflatable member changes a curvature only over a sub-portion of the lens surface. In some embodiments, the regulation mechanism comprises a sealable port for introducing more the fluid into, or drawing some of the fluid out of, the AIOL assembly so as to modify how much the inflatable member inflates. In some embodiments, the adjustment mechanism comprises an inflatable pocket adjacent the extra-capsular-bag interface structure and a sealable port for passing a filling fluid into and out of the inflatable pocket. In some embodiments, the AIOL assembly comprises one or more sealable ports for passing fluid therethrough. In some embodiments, the AIOL assembly comprises one or more haptics extending radially outwards relative to the less rigid portion. In some embodiments, the less-rigid portion and the more-rigid portion are both made of materials that belong to a same class of polymeric materials and are derived from monomers which are mutually compatible. In some embodiments, the less-rigid portion is at least partially convex before application of the pumping force thereto. In some embodiments, the less rigid portion is orientated at an angle relative to the anterior posterior axis of the AIOL assembly. In some embodiments, the more rigid portion is L-shaped, comprising a first leg located anterior to the less rigid portion, and wherein the extension in a posterior direction forms a second leg, the less rigid portion extending between the free ends of the first and second legs respectively.

The present invention seeks to provide a novel AIOL that as a result of its exceptional design, can reach a level of accommodation that can enable patients to see up close, far away and everything in between without glasses.

In accordance with an embodiment of the present invention, the AIOL includes an extra-capsular-bag interface structure, which may serve as haptics and which may be circular in shape, that interfaces with ocular structure external to the capsular bag for implanting the AIOL outside the capsular bag, such as in the space between the iris and the ciliary muscles, known as the sulcus. In one embodiment, the extra-capsular-bag interface structure comprises a tubular ring at least partially filled with a fluid (liquid or gas). The AIOL also includes a central optics assembly, including an inflatable member, such as a membrane, that is connected by one or more fluid conduits to the extra-capsular-bag interface structure. Movement of the ciliary muscle applies a pumping force to cause fluid to flow between the extra-capsular-bag interface structure and the inflatable member in the optics assembly, to change the power of the optics (lens) assembly. The vaulted position changes the optical power to provide the patient with sharp near vision.

The AIOL has a visual enhancement system that exploits the natural accommodation mechanism in the eye to drive the liquid from the perimeter area to the center and to deform the shape of membrane to increase/decrease the power lens assembly.

The AIOL may be implanted outside the capsular bag as an addition lens (e.g., "piggyback lens") on top of an artificial IOL or the natural lens. In the resting position (non-accommodation), the inflatable member is flat (deflated) and the total power of the device is zero. During accommodation, the inflatable member becomes inflated and vaults to provide additional optical power determined by the contraction of the ciliary muscle. The AIOL is a low profile (thickness) AIOL, especially in the central part.

The AIOL of the present invention may be implanted in a phakic patient during cataract surgery and implantation of a non-accommodative IOL (usually in the capsular bag), or in patient that is already pseudo-phakic who has had refractive lens exchange (RLE) and has a non-accommodative IOL (usually in the capsular bag), or in presbyopic patients (usually over the age of 40 who have lost accommodation due to natural lens stiffening) who would like to restore their accommodation capability.

The invention exploits, in a unique way, the ciliary muscle contraction/relaxation to change the power of a lens located in front of a fixed power IOL (pseudo-phakic patients) or in front of the natural crystalline lens (phakic patients). The AIOL of the present invention enables power change, about two diopters and even more, of a lens located in the central part of the AIOL structure.

During the accommodation process, miosis of the iris occurs, and the pupil diameter decreases. Accordingly, the diameter the AIOL may be only about 2-3 mm, although it is not limited to this size.

In accordance with an embodiment of the present invention, the inflatable lens structure includes a plano lens (0 diopters) covered by a membrane in the central part. Alternatively, the lens structure can include another lens power to correct any patient vision problems.

The AIOL may also have a regulation mechanism to adjust the power of the lens and add/remove a few diopters in the unaccommodated state. This adjustment can be done during the implantation procedure or by a separate intervention. Another adjustment can be embedded in the lens design to change the position of the lens structure relative to the ciliary processes to optimize the effect of muscle contraction on the fluid in the extra-capsular-bag interface structure (e.g., the tubular ring). Another adjustment can be embedded in the lens design to change the position of the lens structure along the optical axis and to move the lens structure closer/away from the iris.

BRIEF DESCRIPTION OF THE DRAWINGS

The present invention will be understood and appreciated more fully from the following detailed description taken in conjunction with the drawings in which:

FIGS. 1A and 1B are simplified perspective and side-view illustrations, respectively, of an accommodating intraocular lens (AIOL), constructed and operative in accordance with an embodiment of the present invention, in an unaccommodated state;

FIGS. 2A, 2B, 2C and 2D are simplified perspective, front-view, rear-view, and side-view illustrations, respectively, of the AIOL, in an accommodated state;

FIG. 3 is a simplified side illustration of the AIOL, before and after inflating an inflatable member of an optics assembly of the AIOL, wherein the left side shows the inflatable member before inflation and the right side after inflation;

FIGS. 6A, 6B, 6C and 6D are simplified perspective, front-view, rear-view, and side-view illustrations, respectively, of the AIOL with additional haptics, in accordance with another embodiment of the present invention, in an accommodated state; and FIG. 7 is an enlarged view of a portion of FIG. 3, showing an adjustment mechanism to change a position of the AIOL assembly in accordance with an embodiment of the present invention.

DETAILED DESCRIPTION OF EMBODIMENTS

Reference is now made to FIGS. 1A-3, which illustrate an accommodating intraocular lens (AIOL) assembly 10, constructed and operative in accordance with an embodiment of the present invention.

AIOL assembly 10 includes an optics assembly 12 including an inflatable member 14 that has non-zero optical power when inflated. Optics assembly 12 is shown centrally and axi-symmetrically located in the assembly, but the invention is not limited to this position, and optics assembly 12 may be alternatively located off-center and non-symmetrically located with respect to the optical axis. Without limitation, a diameter of the AIOL assembly 10 may be about 2-3 mm, but other sizes may also be used.

Figure 4A:
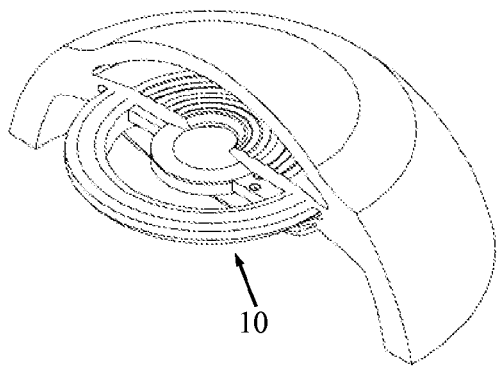
FIGS. 4A, 4B, 4C, 4D and 4E are simplified cutaway perspective, first side-view, second side-view, front-view and rear-view illustrations, respectively, of the AIOL, implanted in an eye.
Figure 4B:
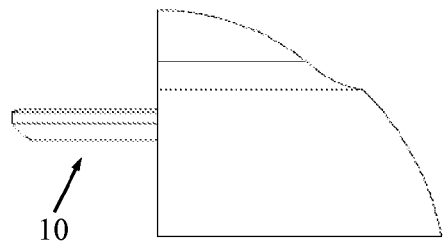
Figure 4C:
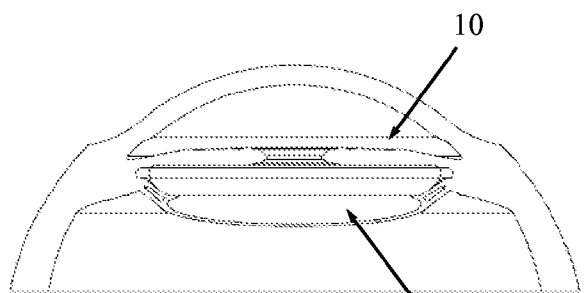
Figure 4D:
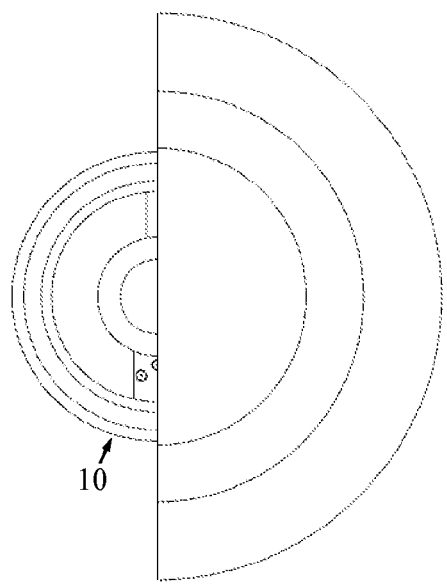
Figure 4E:
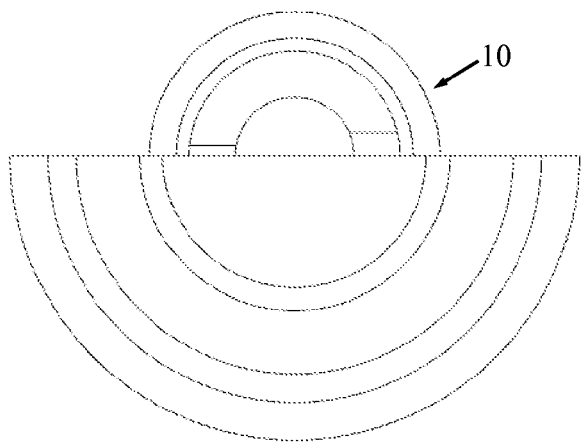
Figure 5A:
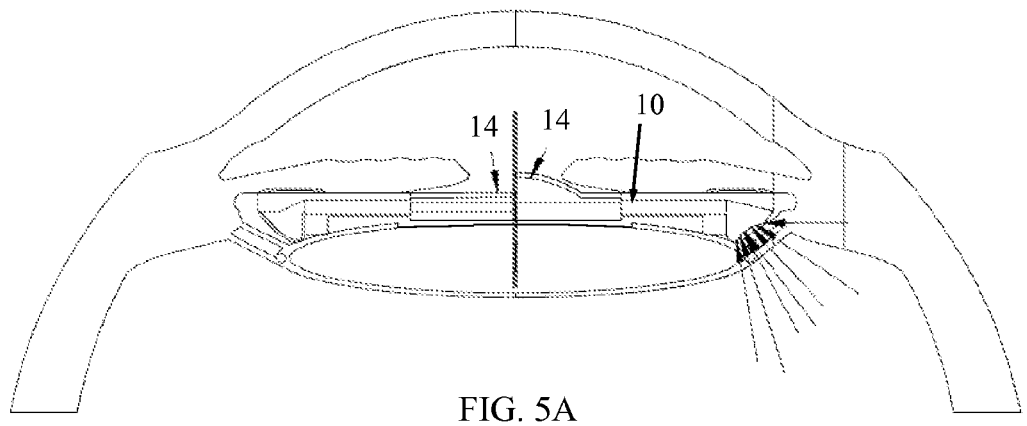
FIGS. 5A, 5B and 5C are simplified cutaway side-view illustrations of the AIOL implanted externally to the capsular bag, wherein respectively, the eye has a natural lens in the capsular bag, an IOL in the capsular bag, and no lens in the capsular bag.
Figure 5B:
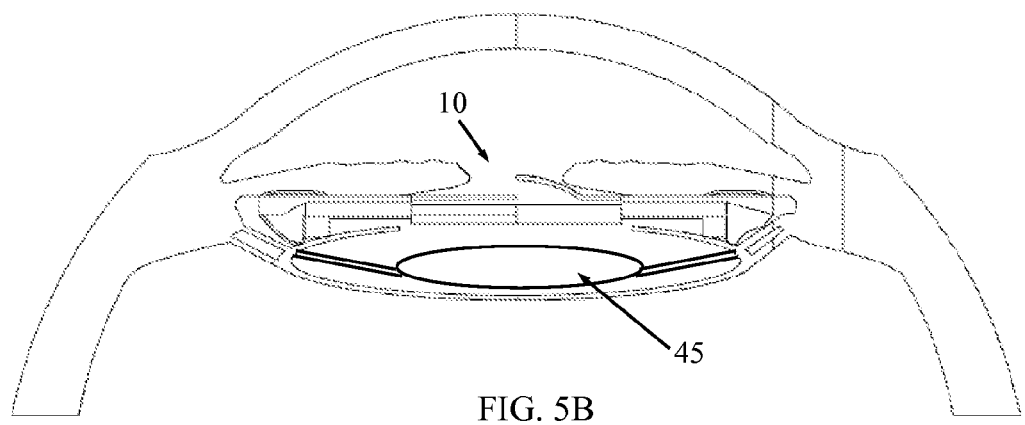
Figure 5C:
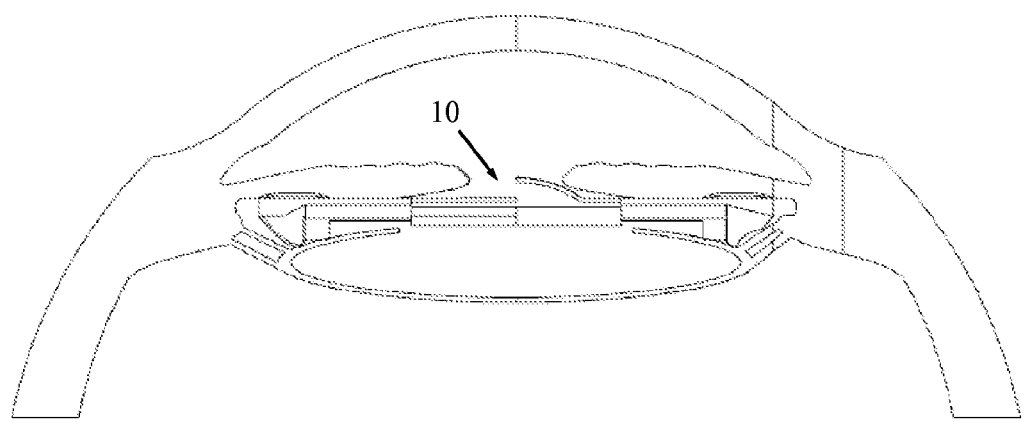

An extra-capsular-bag interface structure 16 is provided for interfacing with ocular structure of the eye external to the capsular bag for implanting the AIOL 10 outside the capsular bag (seen in FIGS. 5A-5C). The extra-capsular-bag interface structure 16 includes a less-rigid portion 18 and a more-rigid portion 20 that define a volume therebetween which is at least partially filled with a fluid 22 and which is in fluid communication with the inflatable member 14 via at least one conduit 24. As seen in FIG. 3, the less-rigid portion 18 is responsive to movement of the ocular structure (indicated by the arrows) to apply a pumping force on the fluid 22 to cause the fluid 22 to flow via the at least one conduit 24 to the inflatable member 14 and change an inflation level of the inflatable member 14 so as to change the optical power of the optics assembly 12.

Reference is made particularly to FIG. 3. The inflatable member 14 includes a plano lens 26 covered by a central membrane 28. The lens structure of the optics assembly 12 may include just the inflatable member 14, or may optionally include another lens 30 with non-zero optic power (with different optical properties or with the same optical properties). The membrane 28 and the additional lens 30 may be located on different faces of the assembly, e.g., on the anterior and posterior faces thereof, separated from each other by at least one conduit 24. It is noted that the inflatable member 14 can be located on either the anterior or posterior portion of the optics assembly 12.

Inflatable member 14 is constructed of a material with sufficient resilience that enables it to expand and increase its convexity upon filling with fluid 22 and contract and decrease its convexity upon evacuation therefrom of fluid 22. Suitable materials include without limitation, silicon-containing polymeric materials, such as hydrophobic and hydrophilic silicone, and others. The lenses of the optics assembly 12 may be spheric, aspheric, toric or other types of optics.

In accordance with an embodiment of the present invention, inflation of the inflatable member 14 changes a curvature only over a sub-portion of the lens surface of central membrane 28. For example, without limitation, the curvature changes over a sub-portion of the lens surface with a diameter of about 3 mm, instead of the full extent of the lens surface of about 4-6 mm. This is a significant advantage that simplifies the design.

In accordance with an embodiment of the present invention, the less-rigid portion 18 and the more-rigid portion 20 of the extra-capsular-bag interface structure 16 are part of an at least partial tubular ring. The term "rigid" refers to the amount of elastic deformation a material undergoes when subjected to a given amount of force: the less elastic deformation the material undergoes due to a given force, the more rigid the material.

The less-rigid portion 18 and the more-rigid portion 20 may be joined to another, or may be separated from one another. The change in rigidity may be abrupt or gradual. In one embodiment of the invention, the less-rigid portion 18 and the more-rigid portion 20 are both made of materials that belong to the same class of polymeric materials and are derived from monomers which are mutually compatible, allowing the materials to be co-cured and/or bonded, for example chemically bonded or otherwise joined, to one another. For example, these materials include, without limitation, acrylic polymeric materials, cross-linked acrylic materials, copolymers of methacrylate and acrylate esters cross-linked with one or more functional acrylate/methacrylate cross-linking components, hydrogels, (e.g., hydroxyethyl methacrylate (HEMA) polymer or methyl methacrylate/N-vinyl pyrrolidone (MMA/NVP) copolymer or the like), silicon-containing polymeric materials, such as hydrophobic and hydrophilic silicone, and others.

In another embodiment, the more-rigid portion 20 may be constructed of a different material than the less-rigid portion 18, such as but not limited to, polymethylmethacrylate (PMMA), collagen, hydrogel, hyaluronic acid, polysulfones, thermolabile materials and other relatively hard or relatively soft and flexible biologically inert optical materials.

As seen in FIG. 3, the less-rigid portion 18 is concave facing away from the inflatable member 14 during application of the pumping force (the less-rigid portion 18 may deform and change its shape in other manners as well). The more-rigid portion 20 remains flat and generally parallel to the deflated plane of the inflatable member 14.

Fluid 22 may include, but is not limited to, water, saline solution, oil, silicone oil and other medically approved liquids, air or other gas, gel or others.

AIOL assembly 10 may include a regulation mechanism 32 to adjust optical power of the optics assembly 12. For example, the regulation mechanism 32 may include a sealable port 36 for introducing more fluid 22 into, or drawing some of fluid 22 out of, AIOL assembly 10 so as to modify how much inflatable member 14 inflates. Another port 37 may be provided for filling the assembly with fluid 22.

Reference is made to FIG. 7, which is an enlarged view of a portion of FIG. 3. AIOL assembly 10 may include an adjustment mechanism 34 to change a position of the AIOL assembly 10 along the optical axis of the eye, or to move the AIOL assembly 10 with respect to the iris of the eye. For example, the adjustment mechanism 34 may include an inflatable pocket 40, which may or may not be adjacent extra-capsular-bag interface structure 16, and a sealable port 42 for passing a filling fluid 44 into and out of inflatable pocket 40. The act of filling pocket 40 with fluid causes the AIOL assembly 10 to move along the optical axis, or to move with respect to the iris.

In the un-accommodated state, the ciliary muscles are relaxed, the tubular ring is un-squeezed and the membrane is flat while the AIOL structure adds no optical power (except for any fixed optical correction, if needed); this is the state for far distance vision. In the accommodated state, the ciliary muscles are contracted, and the tubular ring is squeezed; fluid is pumped towards the inflatable member 14 to vault the membrane and create a dome shape increasing the optical power, such as by a few diopters. This is the state for near distance vision. When the ciliary muscles relax, the fluid flows back to the tubular ring. The optical power change is continuous and controlled by the human brain to reach clear image on the retina.

FIGS. 4A-4E illustrate the AIOL assembly 10 implanted in an eye.

FIG. 5A illustrates the AIOL assembly 10 implanted externally to the capsular bag, in a patient that has a natural lens in the capsular bag.

FIG. 5B (also FIG. 4C) illustrates the AIOL assembly 10 implanted externally to the capsular bag, in a patient that has another IOL 45, such as but not limited to, a capsular bag IOL (however, the other IOL 45 can be outside the bag). In this case, the optics assembly 12 serves as an additional lens to the capsular bag IOL 45. The AIOL structure 10 is shown in front of the capsular bag posterior to the iris, and supported in the sulcus. The extra-capsular-bag interface structure 16 (e.g., the tubular circumferential ring) is held against the ciliary muscles and/or the zonules and/or the capsular bag area in the region of the equator. The AIOL structure can be very thin in its central part, wherein the optics assembly 12 has a thickness of no more than 2 mm when inflatable member 14 is not inflated to its maximum (inflated by any pumping device, not necessarily a less-rigid portion, e.g., a miniature electrical pump), thus being suitable as a piggyback IOL. Alternatively, the optics assembly 12 may have a thickness of no more than 1.5 mm when inflatable member 14 is not inflated to its maximum. Alternatively, the optics assembly 12 may have a thickness of no more than 1 mm when inflatable member 14 is not inflated to its maximum.

FIG. 5C illustrates the AIOL assembly 10 implanted externally to the capsular bag, in a patient that has no lens in the capsular bag.

In the embodiment of FIGS. 6A-6D, AIOL assembly 10 further includes one or more haptics 38.

Relaxation of the ciliary muscles will end by refilling of the tube 19 with liquid drive back by the stretched membrane 12.

Although not necessary to carry out the invention, preferably the same index of refraction should be used for the fluid 22 and the optics assembly 12.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. An accommodating intraocular lens (AIOL) assembly comprising:
   an optics assembly comprising an inflatable member that has non-zero optical power when inflated;
   and an extra-capsular-bag interface structure for interfacing with ocular structure of an eye external to a capsular bag for implanting the AIOL outside the capsular bag, said extra-capsular-bag interface structure comprising a less-rigid portion and a more-rigid portion that define a volume therebetween which is at least partially filled with a fluid and which is in fluid communication with said inflatable member via at least one conduit, and
   wherein said less-rigid portion is responsive to movement of the ocular structure to apply a pumping force on said fluid to cause said fluid to flow via said at least one conduit to said inflatable member and change an inflation level of said inflatable member so as to change the optical power of said optics assembly, and wherein said less-rigid portion is posterior relative to a first portion of said more-rigid portion, posterior defined along an anterior-posterior optical axis of the AIOL assembly, said less-rigid portion is curved and said first portion of said more-rigid portion is flat; said more rigid portion further comprising an extension in a posterior direction which is at a radially inward position relative to said less rigid portion.

2. The AIOL assembly according to claim 1, wherein said less-rigid portion and said more-rigid portion are part of an at least partial tubular ring.

3. The AIOL assembly according to claim 1, further comprising capsular bag IOL, wherein said optics assembly serves as an additional lens to said capsular bag IOL.

4. The AIOL assembly according to claim 1, wherein said inflatable member comprises a plano lens covered by a central membrane.

5. The AIOL assembly according to claim 1, wherein said optics assembly comprises in addition to said inflatable member a lens with non-zero optic power.

6. The AIOL assembly according to claim 1, further comprising a regulation mechanism to adjust optical power of said optics assembly.

7. The AIOL assembly according to claim 6, wherein said regulation mechanism comprises a sealable port for introducing more said fluid into, or drawing some of said fluid out of, said AIOL assembly so as to modify how much said inflatable member inflates.

8. The AIOL assembly according to claim 1, further comprising an adjustment mechanism to change a position of said AIOL assembly along an optical axis of the eye.

9. The AIOL assembly according to claim 8, wherein said adjustment mechanism comprises an inflatable pocket adjacent said extra-capsular-bag interface structure and a sealable port for passing a filling fluid into and out of said inflatable pocket.

10. The AIOL assembly according to claim 1, further comprising an adjustment mechanism to change a position of said AIOL assembly with respect to an iris of the eye.

11. The AIOL assembly according to claim 1, wherein said less-rigid portion is concave facing away from said inflatable member during application of the pumping force, whereas said first portion of said more-rigid portion remains flat and generally parallel to a deflated anterior face of said inflatable member.

12. The AIOL assembly according to claim 1, wherein said inflatable member comprises a lens surface and inflation of said inflatable member changes a curvature only over a sub-portion of said lens surface.

13. The AIOL assembly according to claim 1, further comprising one or more sealable ports for passing fluid therethrough.

14. The AIOL assembly according to claim 1, further comprising one or more haptics extending radially outwards relative to said less rigid portion.

15. The AIOL assembly according to claim 1, wherein said less-rigid portion and said more-rigid portion are both made of materials that belong to a same class of polymeric materials and are derived from monomers which are mutually compatible.

16. The AIOL assembly according to claim 1, wherein said less-rigid portion is at least partially convex before application of the pumping force thereto.

17. The AIOL assembly according to claim 1, wherein said less rigid portion is orientated at an angle relative to said anterior posterior axis of the AIOL assembly.

18. The AIOL assembly according to claim 1, wherein said more rigid portion is L-shaped, with said first portion comprising a first leg located anterior to said less rigid portion, and wherein said extension in a posterior direction forms a second leg, said less rigid portion extending between free ends of said first and second legs respectively.

* * * * *